US008825148B2

(12) United States Patent
Zhang et al.

(10) Patent No.: US 8,825,148 B2
(45) Date of Patent: Sep. 2, 2014

(54) SYSTEM FOR MONITORING AND DIAGNOSIS OF CARDIAC ELECTROGRAM SIGNALS USING MULTI-DIMENSIONAL ANALYSIS

(71) Applicant: Siemens Medical Solutions USA, Inc., Malvern, PA (US)

(72) Inventors: Hongxuan Zhang, Palatine, IL (US); Mikhail Uvarov, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 16 days.

(21) Appl. No.: 13/670,686

(22) Filed: Nov. 7, 2012

(65) Prior Publication Data

US 2013/0190637 A1    Jul. 25, 2013

Related U.S. Application Data

(60) Provisional application No. 61/590,356, filed on Jan. 25, 2012.

(51) Int. Cl.
*A61B 5/044* (2006.01)
*A61B 5/0452* (2006.01)
*A61B 5/0456* (2006.01)

(52) U.S. Cl.
CPC ............ *A61B 5/0456* (2013.01); *A61B 5/0452* (2013.01); *A61B 5/044* (2013.01)
USPC ......................................................... 600/523

(58) Field of Classification Search
CPC ....................................................... A61B 5/044
USPC .................................................. 600/523, 525
See application file for complete search history.

(56) References Cited

U.S. PATENT DOCUMENTS

| 4,136,690 | A | 1/1979 | Anderson et al. |
| 4,989,610 | A | 2/1991 | Patton et al. |
| 5,284,152 | A | 2/1994 | Portnuff et al. |
| 5,301,677 | A | 4/1994 | Hsung |
| 5,474,078 | A | 12/1995 | Hutson |
| 5,645,069 | A | 7/1997 | Lee |
| 5,682,901 | A | 11/1997 | Kamen |
| 5,788,644 | A | 8/1998 | Donehoo et al. |
| 5,956,013 | A | 9/1999 | Raj et al. |
| 6,128,526 | A | 10/2000 | Stadler et al. |
| 6,411,843 | B1 | 6/2002 | Zarychta |
| 6,505,067 | B1 | 1/2003 | Lee et al. |
| 6,741,887 | B1 * | 5/2004 | Gleeson ........................ 600/523 |
| 6,934,578 | B2 * | 8/2005 | Ramseth ....................... 600/523 |
| 7,016,721 | B2 | 3/2006 | Lee et al. |
| 7,113,820 | B2 | 9/2006 | Schlegel et al. |
| 7,184,819 | B2 | 2/2007 | Tabbara et al. |

(Continued)

*Primary Examiner* — George Evanisko
(74) *Attorney, Agent, or Firm* — Brennan K Bradley

(57) ABSTRACT

An analyzer automatically analyzes both, a common portion of multiple successive heart cycles of electrophysiological signal data synchronized with respect to a P wave and a common portion of multiple successive heart cycles of the signal data synchronized with respect to an R wave, to identify changes occurring in amplitude value and time duration of the common portion of the multiple successive heart cycles of the signal data. A display processor initiates generation of at least one display image showing the common portion of the multiple successive heart cycles synchronized in time, adjacent and mutually vertically displaced to facilitate visual comparison and highlighting an identified change by a visual attribute.

21 Claims, 9 Drawing Sheets

(56) References Cited

U.S. PATENT DOCUMENTS

| | | |
|---|---|---|
| 7,194,298 B2 | 3/2007 | Massicotte et al. |
| 7,266,408 B2 | 9/2007 | Bojovic et al. |
| 7,519,416 B2 | 4/2009 | Sula et al. |
| 7,623,910 B2 | 11/2009 | Couderc et al. |
| 7,643,870 B2 | 1/2010 | Kohls |
| 7,751,874 B2 | 7/2010 | Olson |
| 7,751,875 B2 | 7/2010 | Bojovic et al. |
| 7,801,591 B1 * | 9/2010 | Shusterman ............ 600/509 |
| 7,962,201 B2 | 6/2011 | Simske et al. |
| 8,024,030 B2 | 9/2011 | Douglas et al. |
| 8,290,574 B2 | 10/2012 | Feild et al. |
| 2003/0083587 A1 | 5/2003 | Ferek |
| 2009/0088655 A1 * | 4/2009 | Vajdic et al. ............ 600/523 |

* cited by examiner

10

SYSTEM FOR MONITORING AND DIAGNOSIS OF CARDIAC ELECTROGRAM SIGNALS USING MULTI-DIMENSIONAL ANALYSIS

This is a non-provisional application of provisional application Ser. No. 61/590,356 filed Jan. 25, 2012, by H. Zhang et al.

FIELD OF THE INVENTION

This invention concerns a system for analyzing common portions of successive heart cycles of a cardiac electrophysiological signal to identify changes occurring in amplitude value and time duration of the common portion and visually highlighting changes in a display.

BACKGROUND OF THE INVENTION

Electrophysiological signal monitoring including ECG signal and intra-cardiac electrogram monitoring is commonly used for patient health status evaluation. ECG signal morphologies are used to diagnose patient cardiac rhythm and health status. However known analysis and interpretation of a continuous single dimensional ECG waveform is subjective and needs extensive clinical experience for CRM (cardiac rhythm management). CAD (Coronary Artery Disease) and heart-related problems and cardiac arrhythmias are serious health problems. A 12-lead electrocardiogram (ECG) and multi-channel intra-cardiac electrograms (ICEGs) are diagnostic reference standards used for evaluating cardiac rhythm and events. Known waveform morphology and time domain parameter analysis, such as of a P wave, QRS complex, ST segment and T wave, are used for cardiac arrhythmia monitoring and identification, e.g. atrial fibrillation (AF), myocardial ischemia (MI), ventricular tachycardia/fibrillation (VT/VF). However, continuous waveform morphology and time domain parameter analysis is sometimes subjective and time-consuming, and requires extensive expertise and clinical experience for accurate interpretation and proper cardiac rhythm management.

Known clinical methods and approaches for ECG waveform monitoring and diagnosis typically involve 1-dimensional heart beat signal waveform and morphology analysis or involve analysis concerning a 0.1 mV elevation of an ST segment for myocardial ischemia (an ST segment is usually determined by using R wave detection). Furthermore, known ECG waveform analysis typically focuses on the time domain or frequency domain calculation of a single or averaged heart cycle signal. Known clinical diagnosis, monitoring and detection methods, such as Holster monitoring use one dimensional signal comparison and visualization for multi-heart beat signals. These known systems only use R wave synchronization for signal comparison and are unable to track the location of the arrhythmia and are unreliable or insensitive to early small signal changes and variation. Additionally, cardiac electrophysiological activities and signals (ECG and ICEG) are time varying and known signal calculation and related analysis usually is unable to localize a precise malfunction severity and trend of the cardiac events (e.g., of myocardial ischemia and infarction), such as cardiac pathology irregularity stages and arrhythmia occurrence.

Known clinical diagnosis is unable to comprehensively link real time ECG sequential signals and cardiac function, such as ECG signal abnormality with an object in a functional image as an anatomical mapping, which may be used for accurate cardiac arrhythmia localization, type identification, severity characterization, and corresponding clinical treatment. Known ECG and electrophysiological signal monitoring systems usually involve one dimensional waveform morphology analysis of multiple ECG signal channels (such as lead I, II, III, for example). Known ECG and electrophysiological signal diagnosis and evaluation depend on physician and cardiologist experience and knowledge. Known systems also lack criteria for quantitative diagnosis and characterization of a sequential ECG signal trend, especially in an early stage of cardiac events. A system according to invention principles addresses these deficiencies and related problems.

SUMMARY OF THE INVENTION

A system analyzes cardiac electrophysiological signals by employing different kinds of synchronization for sequential multi-dimensional cardiac portion signal comparison and abnormality identification in a corresponding image (X-ray, ultrasound, for example) indicating anatomical structure abnormality severity, location and type. A system analyzes cardiac electrophysiological signals using an acquisition processor for acquiring signal data representing heart electrical activity over multiple heart cycles. An individual heart cycle comprises multiple different signal portions between successive sequential R waves. An analyzer automatically analyzes both, a common portion of multiple successive heart cycles of the signal data synchronized with respect to a P wave and a common portion of multiple successive heart cycles of the signal data synchronized with respect to an R wave, to identify changes occurring in amplitude value and time duration of the common portion of the multiple successive heart cycles of the signal data. A display processor initiates generation of at least one display image showing the common portion of the multiple successive heart cycles synchronized in time, adjacent and mutually vertically displaced to facilitate visual comparison and highlighting an identified change by a visual attribute.

DETAILED DESCRIPTION OF THE INVENTION

Figure 1:
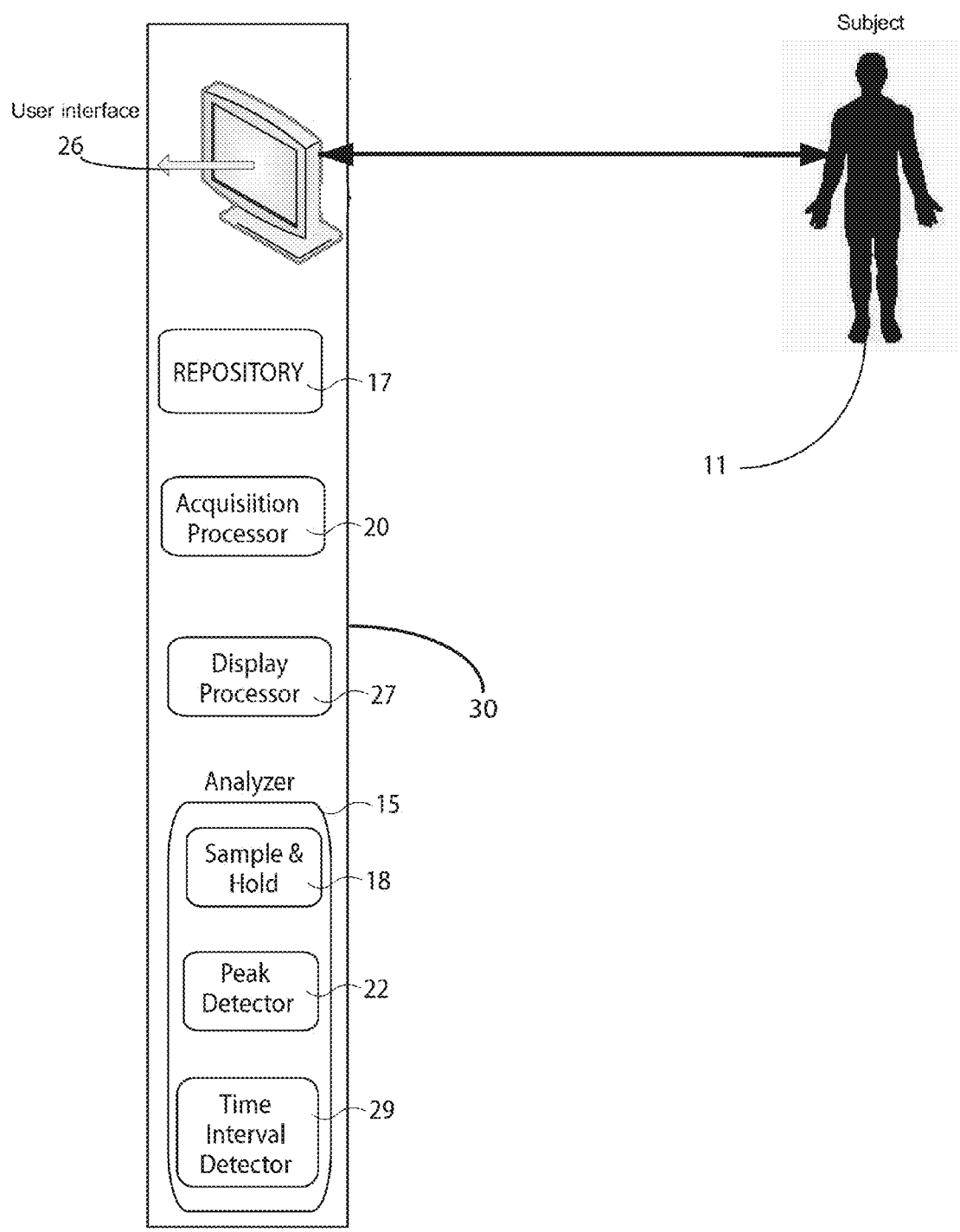
FIG. 1 shows a system for analyzing cardiac electrophysiological signals, according to invention principles.

A system improves analysis and interpretation of cardiac electrophysiological signals for cardiac patient diagnosis and treatment and quantitatively and automatically synchronizes sequential cardiac heart-beat signals for presentation in a multi-dimensional user-friendly visualization interface. The system employs different kinds of waveform and cardiac function signal based synchronization for sequential cardiac portion signal comparison and related calculation. The system further provides real time multi-dimensional cardiac signal monitoring, parameter calculation and mapping to identify heart function status and in conjunction with an image (X-ray, ultrasound, for example) indicates anatomical structure abnormality severity, location and type. The system facilitates monitoring and visualizing heart function, tissue and rhythm disorders, differentiates cardiac arrhythmias, characterizes pathological severity, predicts life-threatening events, and identifies drug delivery effects. Further, the system may be utilized in different types of cardiac arrhythmia detection and characterization, such as myocardial ischemia, ventricular tachycardia, and ventricular fibrillation.

Most cardiac abnormalities and pathological symptoms are slowly emerging and some cardiac arrhythmias are non-symptomatic and usually last a period of time before abnormal electrophysiological signal (both ECG and ICEG) demonstrate significant changes, such as ST segment elevation in excess of 0.1 mV indicating ischemia. Consequently, known clinical systems fail to efficiently detect and characterize a problem, especially in an early stage of cardiac events. In addition, different kinds of cardiac diseases may affect different parts of cardiac tissue. Atrial fibrillation distorts P wave morphology and myocardial ischemia changes an ST segment level, for example.

A system according to invention principles employs different kinds of synchronization information, such as by using P wave synchronization (associated with ventricular function), pacing pulse synchronization for R wave ventricular depolarization function abnormality tracking and S wave synchronization for T wave ventricular repolarization pathology detection, for example. The system provides multi-dimensional sequential dynamic ECG monitoring and data visualization and modeling with automatic and adaptive synchronization for different portions of cardiac tissue and function diagnosis. The system also provides an ECG/ICEG signal workflow and real time mapping between electrophysiological signals and image features provided by an image system, such as an X-ray, fMRI (functional MRI), ultrasound image system. The system calculates T wave and S wave small timing-latency variation based on P wave synchronization between different beats. The system also provides trend diagnosis for pacing synchronization in pacing cases and other cardiac wave based heart beat trend diagnosis in non-pacing cases and provides statistical analysis for sequential function severity and function trend analysis for a region of interest (ROI) of cardiac tissue. The system adaptively applies different criteria and standards in ECG signal analysis, in response to a detected patient ECG signal trend, environment noise, clinical application and procedure being performed.

FIG. 1 shows system 10 for analyzing cardiac electrophysiological signals. Server 30 includes user interface 26, analyzer 15, acquisition processor 20, display processor 27 and repository 17. Analyzer 15 includes sample and hold unit 18, peak detector 22 and time interval detector 29. User interface 26 comprises a graphical user interface (GUI) presented on a display together with a keyboard, mouse, touchscreen or voice recognition device, for example, for user data and command entry into system 10. Patient monitoring signals including ECG, ICEG, blood pressure, SPO2 and other vital sign signals, are acquired from patient 11 buffered, filtered, amplified, digitized and processed by acquisition processor 20.

Acquisition processor 20 acquires signal data representing heart electrical activity over multiple heart cycles. An individual heart cycle comprises multiple different signal portions between successive sequential ECG R waves; Analyzer 15 automatically analyzes both, a common portion of multiple successive heart cycles of the signal data synchronized with respect to a P wave and a common portion of multiple successive heart cycles of the signal data synchronized with respect to an R wave. Thereby analyzer 15 identifies changes occurring in amplitude value and time duration of the common portion of the multiple successive heart cycles of the signal data. Display processor 27 initiates generation of at least one display image showing the common portion of the multiple successive heart cycles synchronized in time, adjacent and mutually vertically displaced to facilitate visual comparison and highlighting an identified change by a visual attribute.

System 10 performs sequential multi-dimension electrophysiological signal monitoring and visualization, with automatic and adaptive synchronization and real time calculation and adaptive function mapping between electrophysiological signals and an image object identified in an image provided by an imaging system. The image provides medical condition feature visualization and identifies a diagnosis.

Figure 2:
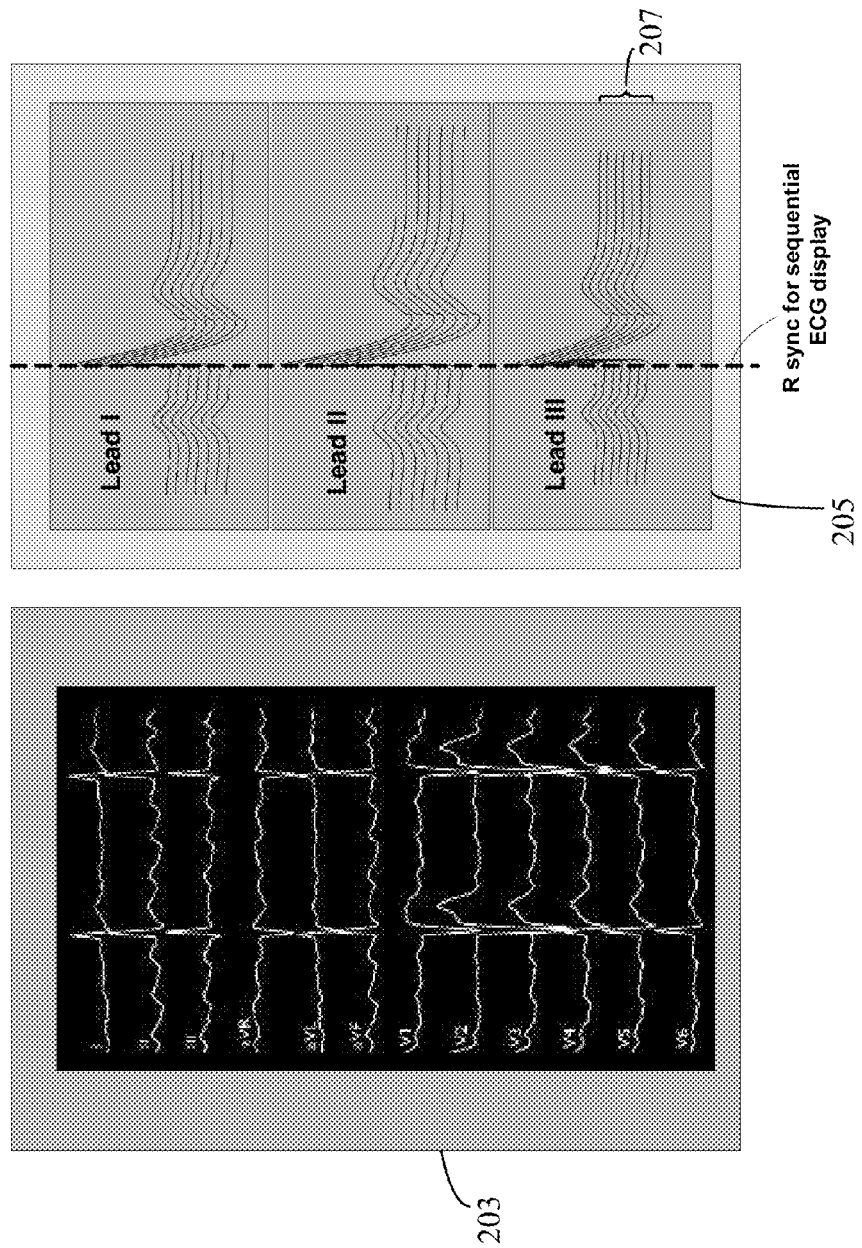
FIG. 2 shows known monitored one dimensional clinical ECG waveform and two dimensional sequential ECG sweep signal visualization, according to invention principles.

FIG. 2 shows a comparison of known monitored one dimensional clinical ECG waveforms 203 and system 10 two dimensional sequential ECG sweep signals 205 (with R wave synchronization) visualization. The known one dimensional waveform morphology monitoring illustrated in waveform 203 requires extensive clinical knowledge for interpretation and needs the use of smart functions for time latency and amplitude measurement. System 10 performs real time monitoring and presents ECG signal sweeps e.g. sweep 207 showing the latest seven superimposed waveforms of successive heart cycle ECG lead III waveforms advantageously enabling, a user to identify small changes in signal timing and latency, which may be cardiac pathology related. The system 10 two dimensional sequential ECG sweep monitoring adaptively selects a synchronization method from multiple different methods for different portion cardiac tissue and function analysis. The timing synchronization methods include use of R wave synchronization and P wave timing synchronization to track and monitor ventricular abnormality, for example. The system 10 two dimensional sequential continuous ECG sweep signals 205 shows sequential ECG monitoring for lead I, II, III, for example, with an individual sweep signal covering one ECG heart cycle.

Figure 3:
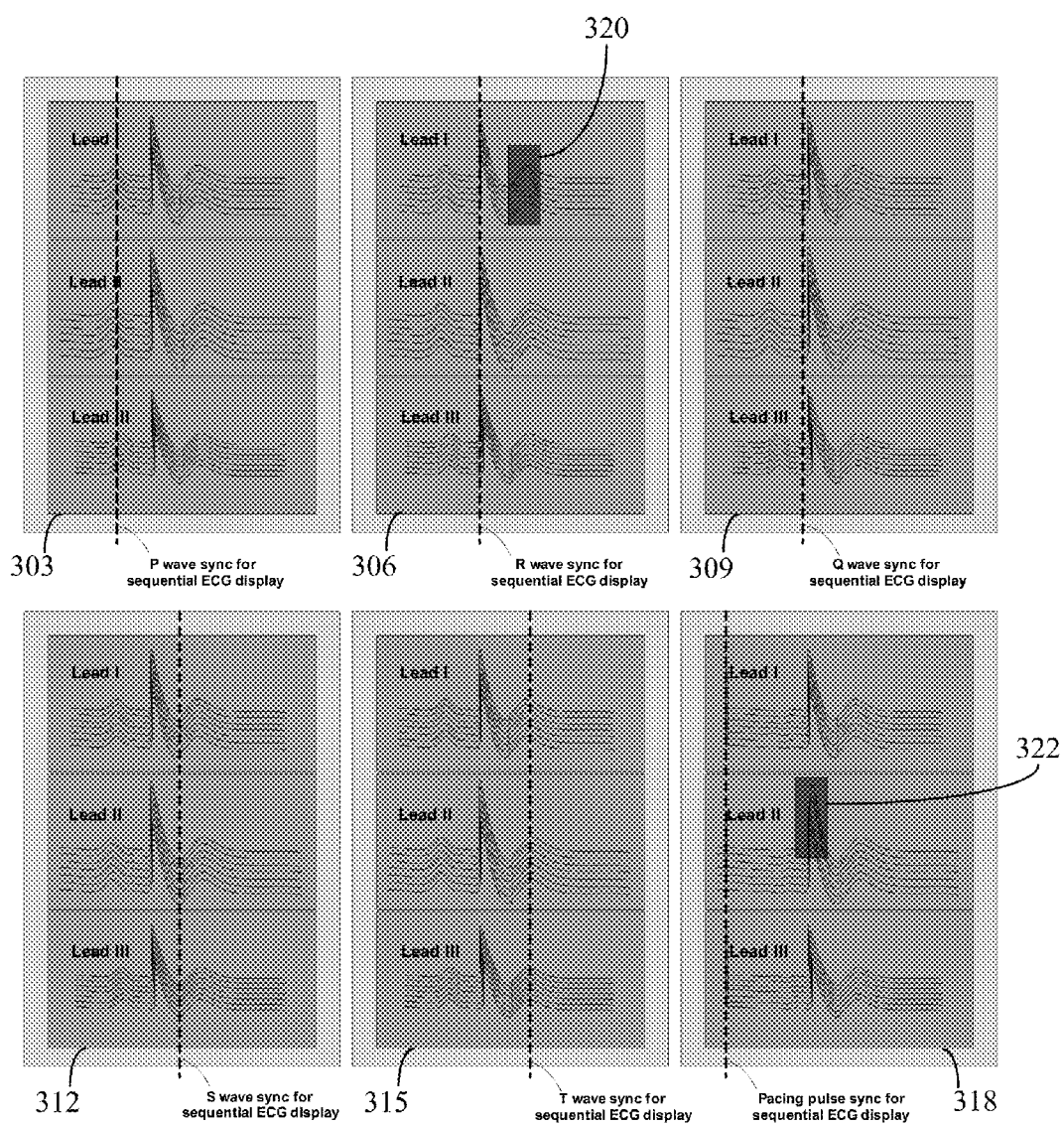
FIG. 3 shows a visualization method tree for P wave, Q wave, R wave, S wave, T wave and Pacing pulse synchronization for ECG signal monitoring, according to invention principles.

FIG. 3 shows a visualization tree showing ECG lead I, II, III signals synchronized by P wave 303, R wave 306, Q wave 309, S wave 312, T wave 315 and Pacing pulse 318, for example, for monitoring. System 10 adaptively selects one of a P wave, Q wave, R wave, S wave, T wave, Pacing pulse signal for ECG synchronization based on data indicating a clinical situation and procedure and cardiac function to be monitored. The amplitude variation is shown in superimposed successive waveform distribution while the timing and latency variation is shown in the waveform morphology (peak, shape, for example), similarity, timing synchronization and waveform shift, for example. Three leads are shown but other numbers of leads can readily be presented including leads internal and external to a patient. In addition, the system sequential cardiac multi-sweep diagnosis facilitates capture and quantification of morphology changes, such as a fast rising waveform portion of a Q wave to R wave and facilitates QR morphology variation detection and visualization.

System 10 selects between different waveform peak times for use in sequential ECG cycle synchronization comparison and monitoring for multiple individual cycle sweeps of ECG signals. In another embodiment, a sweep has a different length which may be adaptively extended in response to data identifying a clinical application, such as 1 sweep covering 2 or 3 heart cycles for diagnosis and comparison. For example, in FIG. 3, data length of lead II is longer than data length of other leads, which provides flexibility for comparison and better visualization. Similarly, system 10 uses sequential synchronization for pacing cases, and uses pacing pulse 318 waveform synchronization to identify small changes in R wave latency such as in lead II R wave peak time variation.

ECG lead I, II, III signals synchronized with an R wave 306 peak timing stamp show a T wave series 320 indicating a non-uniform signal waveform distribution. The amplitude and latency variety and non-harmonic distribution shows the functionality and electrophysiological response changes in cardiac rhythm and tissue functions. Superimposed synchronized ECG waveform portions are continuously analyzed using an amplitude detector (e.g. peak detector as known) and time interval detector (e.g. clock counters triggered from a portion boundary or peak) to find discrepancies between overlaid waveform portions. Changes in amplitude and time interval (latency) between waveforms are compared to predetermined thresholds and ranges to identify potential medical conditions. The detection uses adaptive and automatic signal monitoring, diagnosis and characterization involving different kinds of signal portion synchronization and gating methods. ECG lead I, II, III signals synchronized with a pacing signal 318 shows an R waveform abnormality 322 which typically occurs in ICD (intra-cardiac defibrillator) patients or operating room (OR) patient with stimulation treatment.

Figure 4:
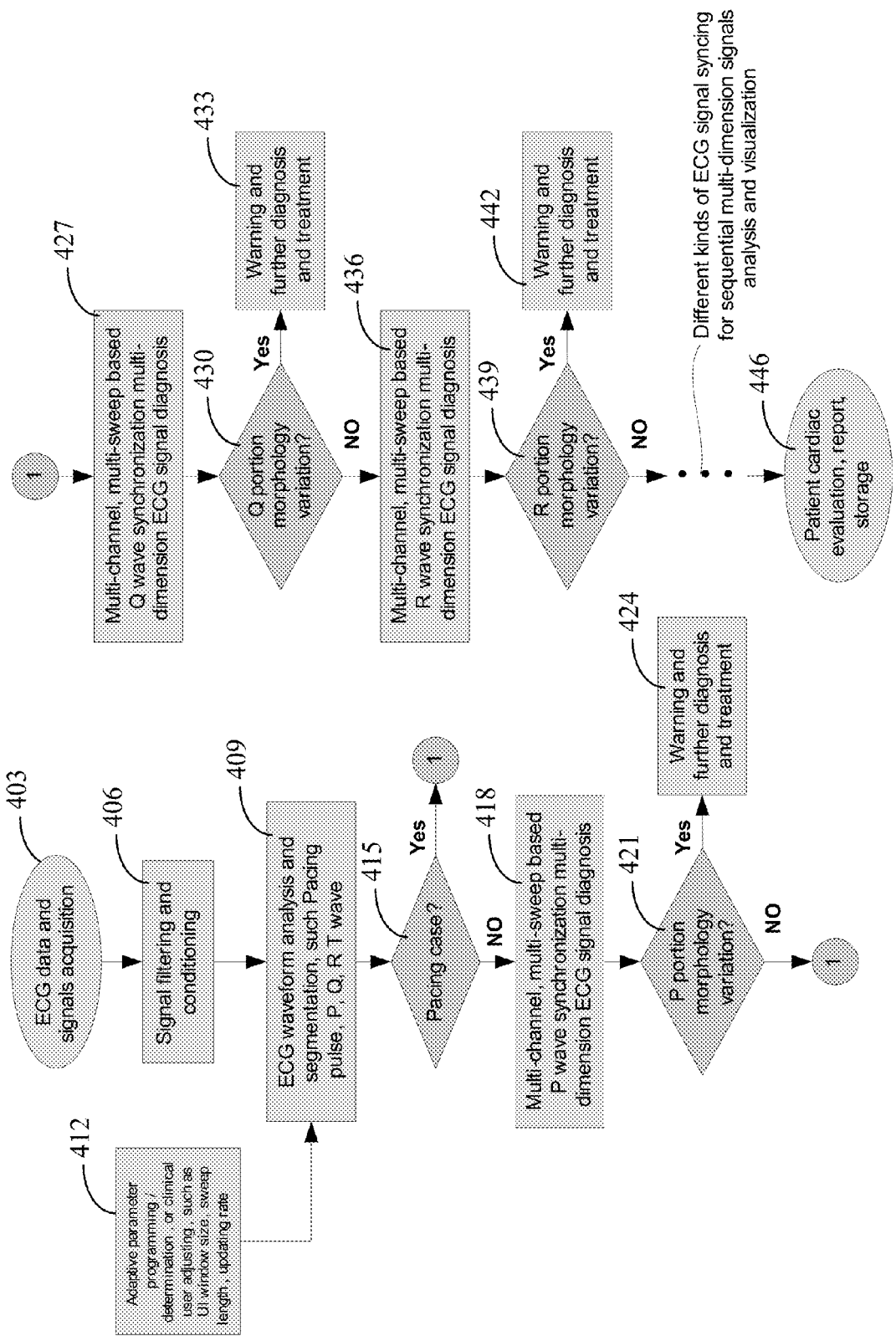
FIG. 4 shows a flowchart of a process of a synchronization method for cardiac signal portion activity diagnosis, according to invention principles.

FIG. 4 shows a flowchart of a process of a synchronization method for cardiac signal portion activity diagnosis performed by system 10. The system uses different kinds of synchronization based sequential ECG signal monitoring to locate pathological tissue, characterize severity, quantify malfunction type, predict a pathology pattern and determine treatment, for example. Analyzer 15 buffers, filters, digitizes and conditions an ECG (or ICEG) signal in step 406 following the start at step 403. Analyzer 15 in step 409 detects P wave, Q wave, R wave, T wave, S wave and U waves of the conditioned ECG signal data by detecting peaks within the received data using a known peak detector and by segmenting a signal represented by the received data into windows where the waves are expected and by identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The signal processor includes a timing detector for determining time duration between the signal peaks and valleys. The time detector uses a clock counter for counting a clock between the peak and valley points and the counting is initiated and terminated in response to the detected peak and valley characteristics. In step 412, analyzer 15 is configured for sweep analysis, user interface window size, sweep data length and update rate.

Analyzer 15 captures sequential cardiac signal sweeps comprising synchronized superimposed ECG signal portions and presents them in a display image via user interface 26 to enable a user to identify and track small changes in ECG (and ICEG) amplitude, timing, latency, and morphology. If analyzer 15 determines an ECG sweep is normal based on P wave synchronization, an ECG sweep based on Q wave synchronization is analyzed followed by analysis successively of sweeps synchronized based on R, S, T and U waves (or in a different order). Analyzer 15 identifies pathology location and timing, to facilitate treatment in response to detection of a sweep abnormality. Analyzer 15 provides a signal sweep comprising a superimposed ECG morphology segment sequence used for cardiac tissue electrophysiological conduction activity diagnosis, by synchronization successively with a pacing pulse, P wave, Q wave, R wave, S wave, T wave, U wave, for example, in steps 418-446.

In response to a determination in step 415 that a non-pacing analysis is to be performed, analyzer 15 in step 418 captures ECG multi-lead channel signal sweeps of a superimposed ECG morphology segment sequence by synchronization with a P wave. In step 421, analyzer 15 analyzes the sweeps to detect amplitude and timing variation within segments of the sweeps indicating a cardiac condition and generates a warning and prompts a user with a candidate treatment in step 424.

If no variation is found in step 421, analyzer 15 in step 427 captures an ECG multi-lead channel signal sweep of a superimposed ECG morphology segment sequence by synchronization with a Q wave. In step 430, analyzer 15 analyzes the sweep to detect amplitude and timing variation within segments of the sweep indicating, a cardiac condition and generates a warning and prompts a user with a candidate treatment in step 433. If no variation is found in step 430, analyzer 15 in step 436 captures an ECG multi-lead channel signal sweep of a superimposed ECG morphology segment sequence by synchronization with an R wave. In step 439, analyzer 15 analyzes the sweep to detect amplitude and timing variation within segments of the sweep indicating a cardiac condition and generates a warning and prompts a user with a candidate treatment in step 442. In similar fashion to the P wave, Q wave and R wave synchronized analysis of steps 418-442, analyzer 15 captures and analyzes an ECG multi-lead channel signal sweep synchronized in response to an S wave, T wave and U wave. In step 446 analyzer 15 outputs and stores a cardiac condition report and the process of FIG. 4 terminates.

The time of occurrence of an abnormality is used to track an event sequence and abnormality location inside cardiac tissue. For example, in a normal case, in a P wave synchronized sequential sweep comparison, if a Q wave is also synchronized for atrial function and ventricular and atrial function are normal, there is no problem. In order to interpret R wave peak synchronization, if amplitude or latency distribution shows some variation, which means ventricular depolarization has some malfunction, this enables a condition to be addressed earlier.

Figure 5:
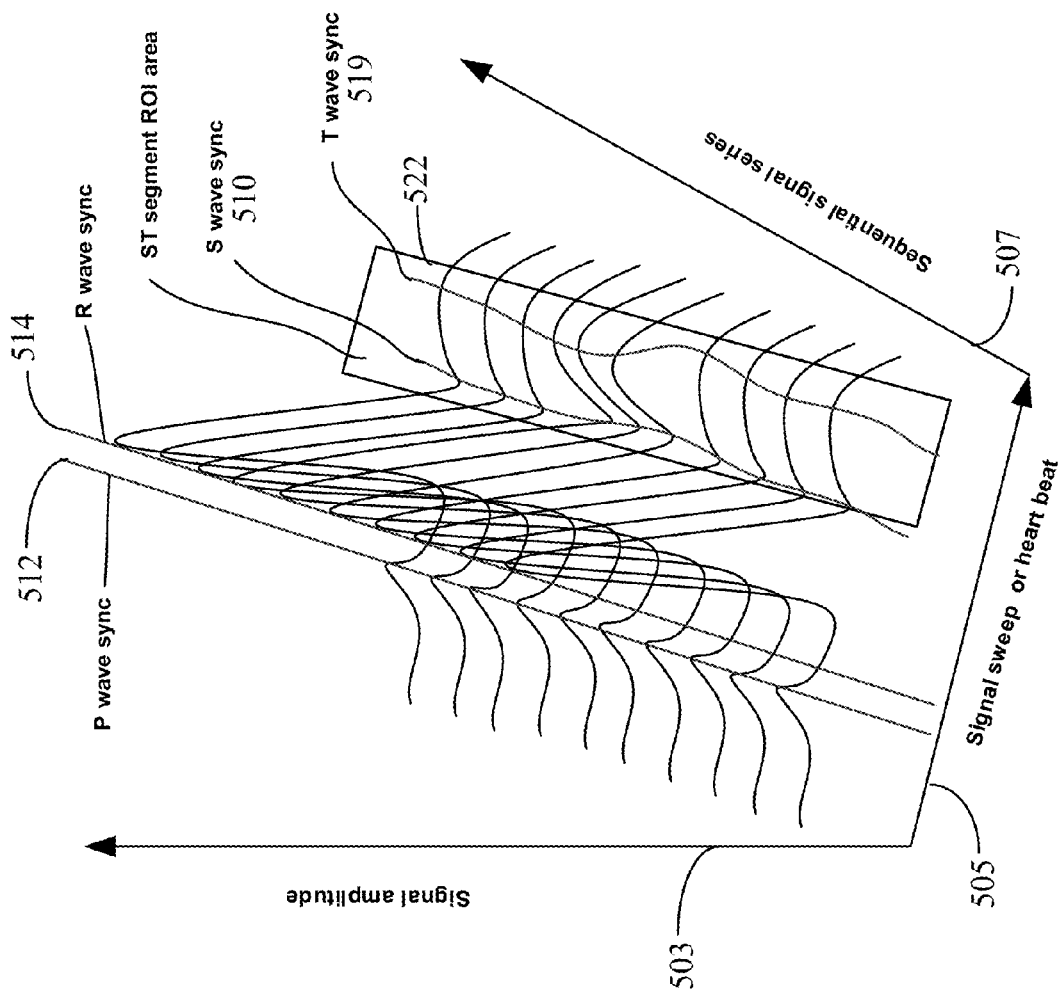
FIG. 5 shows a single lead (lead II) 3-dimensional sequential ECG signal monitoring visualization, according to invention principles.

FIG. 5 shows a single lead (lead II) three dimensional (3D) sequential ECG signal monitoring visualization provided by system 10 (FIG. 1) in response to performing sequential ECG 3D sweep analysis. A two dimensional (2D) ECG sequential sweep presents superimposed waveform portions a predetermined distance apart. A 3D sequential ECG sweep waveform morphology analysis advantageously uses different kinds of parameters, such as amplitude, energy, frequency peak, complexity, for example, as a third axis of data. FIG. 5 shows a 3D sequential ECG waveform sweep analysis with amplitude presented on axis 503, time on axis 505 and sequential ECG portions shown along axis 507, to identify early status of myocardial ischemia. For improved visualization of the multi-dimension ECG sequential signals, color coded data and points are used to indicate an amplitude range and distribution, such as red color to show a sweep out of normal range (the deeper the color, the more out of range). Lines 510 and 519 (e.g. depicted in a color such as red), emphasize variation in amplitude and timing of amplitude peaks of S and T waves.

A presented ECG signal portion is at least one heart cycle signal with full peaks and a sequential signal series comprises continuous successive heart cycle ECG signals or comprises successive heart cycle ECG signal portions from different heart signal episodes that are selected for sequential ECG signal comparison and statistical analysis. The amplitude shown in the third dimension may be color coded to represent amplitude range. The sequential ECG signal sweeps are displayed and compared in the same 3 dimensional window to show early change in data, signals and morphology for a sporadic short acute myocardial ischemia event, which may last 2 to 10 seconds. Usually normal one dimensional ECG continuous waveform monitoring is unable to identify this type of short event. The 3D sequential signal monitoring, indicates a peak series of P waves from different sweeps are lying on the same line 512 with no distortion, a series of R wave peak are also in normal linear mode on line 514 but the ST segment morphology in the middle of sequential signal sweep series shows variation in lines 510 and 519 indicating ST segment morphology variation due to myocardial ischemia events. After 5-10 seconds, the ST segment morphology returns to normal mode.

System 10 adaptively selects different parameters, in response to a type of examination being performed, for detection of nonlinear morphology and shape changes and to identify location, type, timing and severity of a condition using a sequential 3D ECG data series. The time window for each ECG portion in one embodiment is one cardiac heart cycle and the sequential display window along axis 507 shows a sweep of 10 ECG heart cycle portions. The time duration between two sweeps in the sequential ECG waveform can be adaptively controlled without event or ECG waveform distortion, the duration may be 2-5 seconds, for example. If there is distortion in the signals and data, the duration is automatically switched to 1 second, for example. This adaptive method optimizes signal monitoring with efficient sensitivity, accuracy and reliability. In one embodiment, in order to facilitate calculation of the distortion of the sequential morphology sweep signals, a least mean squares method is used for individual points of a region of interest (ROI), such as of P wave synchronization line 512, R wave synchronization line 514, for example. Different kinds of distribution thresholds are predetermined for different severity calculations and warnings, such as 1%, 10%, and 20% changes for early detection of a range of cardiac events from minor to severe.

In ECG waveform sequential analysis performed by analyzer 15, a target model is a linear line. The least mean square analysis is adjusted for use as a deviation analysis. Assume the P wave synchronization line 512 is a mean line, and distance between different P wave peak points and P wave synchronization line 512 indicates deviation or error. In this way, the nonlinearity (distribution error) is defined by following equation:

Nonlinearity of Waveform Peak Series:

$$nonlinearity = \frac{\sqrt{\sum_{i \in sequential\_window\_size}(x_i - E)^2}}{E}$$

In which, E is a mean value of a sequential ECG series of a selected ROI wave peak (or other) point for analysis; $x_i$ is the ROI wave peak point amplitude or timing value. Hence analyzer 15 uses this equation to calculate error distribution and nonlinearity of P wave, R wave, and other wave peak points or a ROI selected point in the sequential monitoring window and applies 1%-20% thresholds to determine severity of changes. In FIG. 5, the nonlinearity of P wave synchronization sequential series (along line 512) is less than 1% while the nonlinearity of the T wave synchronization sequential line 519 shows greater than 15% changes. This may indicate early myocardial ischemia events. In Addition, different methods for ST segment sequential analysis are derived by using a marked area (e.g. area 522) as an ST segment ROI area, between an S wave and T wave synchronization line. The method is applied to a multi-data point sequence for cardiac event detection. Different sequential hypothesis tests, such as at test, for example, are used for confidence determination and are used to control analysis to detect ECG signal changes in a sequential window.

Figure 6:
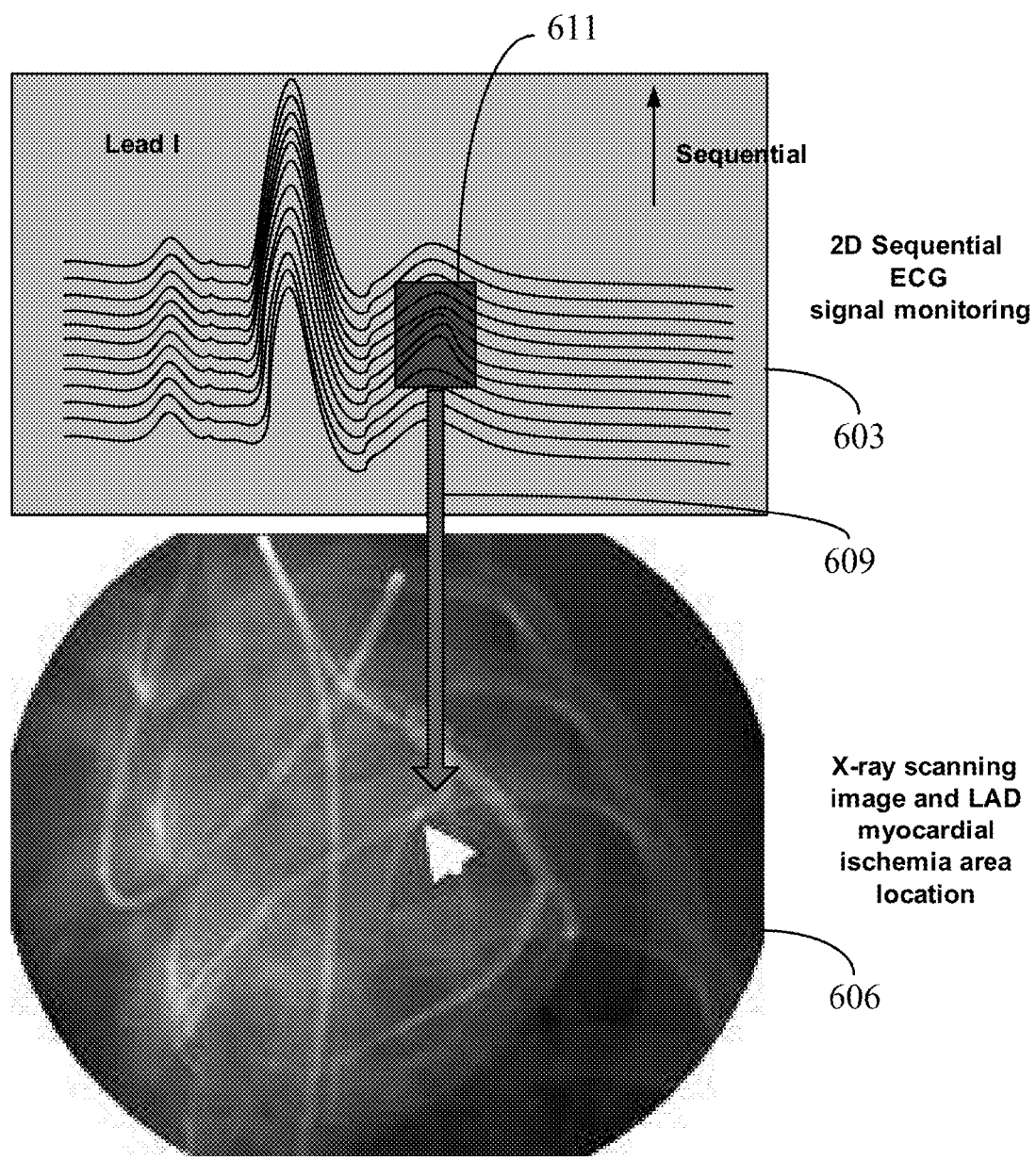
FIG. 6 shows acute myocardial ischemia events with 2-dimensional sequential ECG monitoring and real time mapping to an X-ray image for dual visualization based patient cardiac status analysis, according to invention principles.

FIG. 6 shows acute myocardial ischemia events with 2-dimensional sequential ECG monitoring and real time mapping to an X-ray image for dual visualization based patient cardiac status analysis. System 10 performs multi-dimensional sequential ECG signal monitoring and visualization together with image mapping to track and diagnose location, cardiac function and predict potential emergence of events. ECG signals 603 of one ECG lead are mapped 609 to X-ray image 606 by using ECG sequential analysis calculation results to identify location in image 606 and condition severity. This method combines two real time information acquisition systems, which facilitates diagnosis and determination of clinical treatment with least time delay. P wave, R wave, and S wave portions of signals 603 have negligible signal distortion in the sequential analysis. However the distribution for ST segment and T wave ROI portion 611 shows a big distortion during balloon inflation testing in a Percutaneous transluminal coronary angioplasty (PTCA) study. This shows that sequential ECG distribution analysis used together with imaging analysis for heart status monitoring determines real anatomical causes. PTCA X-ray image 606 is acquired during short term balloon inflation testing (3-5 seconds) and the sequential ECG monitoring shows catheter existence and inflation degrees. Hence by using Sequential ECG monitoring, the severity, type, timing and duration of cardiac ischemia events is quantitatively calculated for cardiac myocardial ischemia treatment workflow and diagnosis. Multiple cardiac signal waveforms are advantageously superimposed in a window with different sequences of cardiac function and activity alignment and synchronization.

System 10 advantageously displays patient signals, especially cardiac functional waveforms (such as of a surface ECG) in multiple-dimensions. For example, a 2-dimensional ECG signal shows superimposed one dimensional signal waveforms separated by a calibrated spatial distance between each waveform as shown in waveforms 205 of FIG. 2. System 10 provides a three dimensional ECG waveform display as in FIG. 5 and shows ECG calculated values for a two dimensional signal waveform series, including signal amplitude, signal energy, signal complexity, signal instantaneous frequency-spectrum, signal latency, for example. Three dimensional ECG waveforms show additional signal properties and characteristics which are reliably and sensitively captured and quantified by the system.

Figure 7:
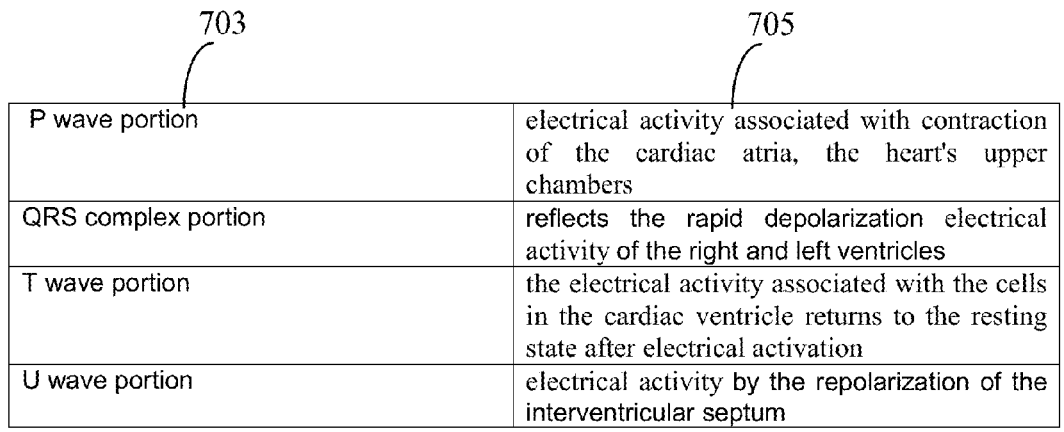
FIG. 7 shows a Table associating heart regions and ECG waveform portions, according to invention principles.
Figure 8:
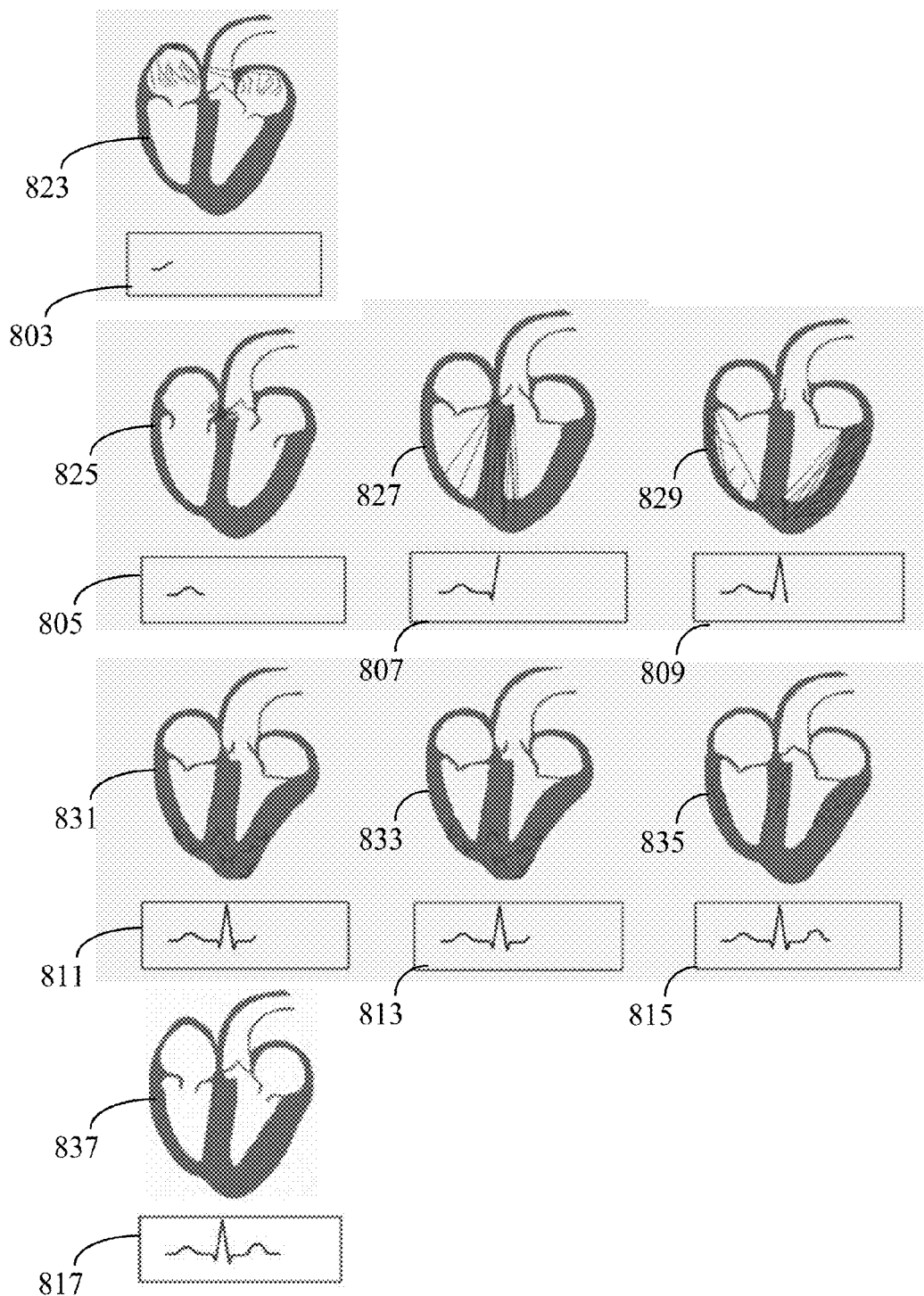
FIG. 8 shows ECG waveform timing and corresponding function position, according to invention principles.

FIG. 7 shows a Table associating heart regions identified in column 705 and ECG waveform portions identified in column 703. FIG. 8 shows ECG waveform timing and corresponding function position. Specifically, FIG. 8 shows current points in received ECG waveforms points 803, 805, 807, 809, 811, 813, 815 and 817 and corresponding heart location and function diagrams 823, 825, 827, 829, 831, 833, 835 and 837.

Figure 9:
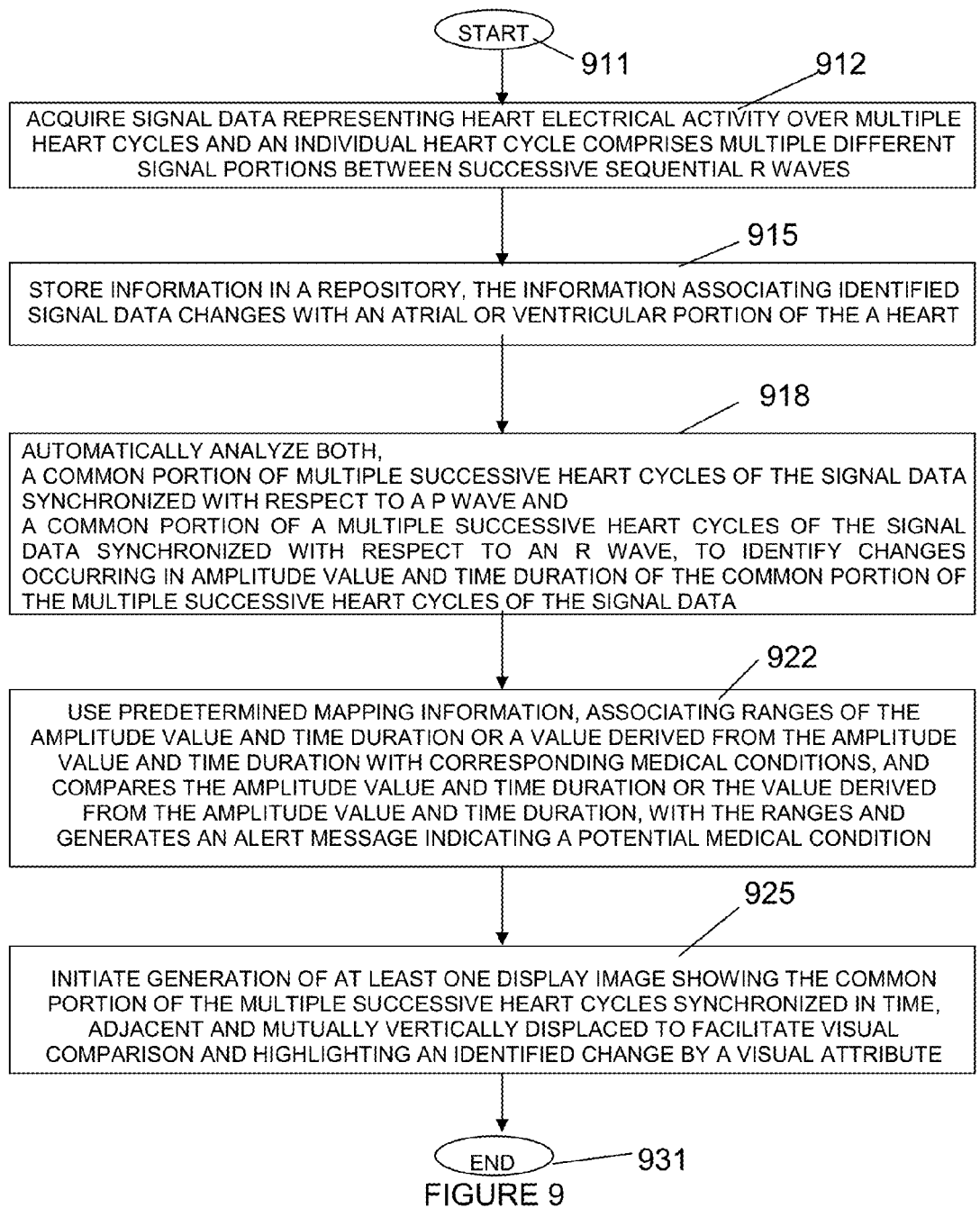
FIG. 9 shows a flowchart of a process used by a system analyzing cardiac electrophysiological signals, according to invention principles.

FIG. 9 shows a flowchart of a process used by system 10 (FIG. 1) for analyzing cardiac electrophysiological signals. In step 912 following the start at step 911, acquisition processor 20 acquires signal data representing heart electrical activity over multiple heart cycles. An individual heart cycle comprises multiple different signal portions between successive sequential R waves. In step 915, analyzer 15 stores in repository 17, information associating identified signal data changes with an atrial or ventricular portion of a heart and an interventricular portion of a heart. In step 918 analyzer 15 automatically analyzes both, a common portion of multiple successive heart cycles of the signal data synchronized with respect to a P wave and a common portion of multiple successive heart cycles of the signal data synchronized with respect to an R wave, to identify changes occurring in amplitude value and time duration of the common portion of the multiple successive heart cycles of the signal data. The common portion comprises one or more whole heart cycles or a portion less than a whole heart cycle. Analyzer 15 automatically sequentially analyzes the common portion of the multiple successive heart cycles of the signal data synchronized with respect to a Q wave, S wave, T wave, U wave as well as the P wave and the R wave.

Analyzer 15 automatically uses the information in identifying a medical condition is associated with an atrial or ventricular portion of a heart in response to the identified change being associated with a P wave or a QRS complex. The analyzer also automatically uses the information in identifying a medical condition is associated with an interventricular portion of a heart in response to the identified change being associated with a U wave. Analyzer 15 in one embodiment includes, a signal sample and hold unit, a peak detector for detecting signal peaks and a time interval detector using a clock counter triggered from a synchronizing P wave or R wave peak detected by the peak detector. The analyzer automatically analyzes the common portion by comparing amplitude values captured by the sample and hold unit at corresponding time points of multiple successive synchronized heart cycles of the signal data. In another embodiment, the time interval detector using a clock counter triggered by a synchronizing P wave or R wave peak detected by the peak detector and terminating a count in response to an identified signal characteristic. The analyzer automatically analyzes the common portion by comparing time intervals associated with one of multiple different portions of a heart cycle. Analyzer 15 also identifies a nonlinearity change occurring in the common portion of the multiple successive heart cycles of the signal data.

Analyzer 15 in step 922 uses predetermined mapping information, associating ranges of the amplitude value and time duration or a value derived from the amplitude value and time duration with corresponding medical conditions, and compares the amplitude value and time duration or the value derived from the amplitude value and time duration, with the ranges and generates an alert message indicating a potential medical condition. The predetermined mapping information associates ranges of the amplitude value and time duration or a value derived from the amplitude value and time duration with particular patient demographic characteristics and with corresponding medical conditions and the analyzer uses patient demographic data including at least one of, age weight, gender and height in comparing the amplitude value and time duration or a value derived from the amplitude value and time duration with the ranges and generating an alert message indicating a potential medical condition. In one embodiment, analyzer 15 uses predetermined mapping information, associating thresholds of the amplitude value and time duration or a value derived from the amplitude value and time duration with corresponding medical conditions, and compares the interval parameter or the value derived from the interval parameter, with the thresholds and generates an alert message indicating a potential medical condition.

In step 925, display processor 27 initiates generation of at least one display image showing the common portion of the multiple successive heart cycles synchronized in time, adjacent and mutually vertically displaced to facilitate visual comparison and highlighting an identified change by a visual attribute. The visual attribute comprises at least one of, (a) color, (b) highlighting, (c) shading, (d) a symbol and (e) text. Further, display processor 27 indicates in a medical image an atrial or ventricular portion of a heart in response to identifying the medical condition. At least one display image shows the common portion of the multiple successive heart cycles in 3-dimensions with the third dimension at least one of, (i) separating individual common portions of successive heart cycles and (ii) showing a signal property comprising at least one of, (a) signal energy, (b) signal complexity, (c) signal instantaneous frequency spectrum and (d) signal latency. The process of FIG. 9 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g. enhancing contrast).

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system uses different kinds of waveform and cardiac function signal based synchronization for superimposed sequential cardiac portion signal comparison in a multi-dimensional visualization, that is used in conjunction with an image (X-ray, ultrasound, for example) to indicate anatomical structure abnormality, severity, location and type. Further, the processes and applications may, in alternative embodiments, be located on one or more (e.g., distributed) processing devices on a network linking the units FIG. 1. Any of the functions and steps provided in FIGS. 1-9 may be implemented in hardware, software or a combination of both. No claim element herein is to be construed under the provisions of 35 U.S.C. 112, sixth paragraph, unless the element is expressly recited using the phrase "means for."

What is claimed is:

1. A system for analyzing cardiac electrophysiological signals, the system comprising:
   an acquisition processor for acquiring signal data representing heart electrical activity over a plurality of heart cycles, an individual heart cycle comprising a plurality of different signal portions between successive sequential R waves;
   an analyzer for
      automatically analyzing both,
         a first sweep based on a common portion of a plurality of successive heart cycles of the signal data, wherein the successive heart cycles in the first sweep are synchronized with respect to a P wave, and
         a second sweep based on the common portion of the plurality of successive heart cycles of the signal data, wherein the successive heart cycles in the second sweep are synchronized with respect to an R wave, and
      said analyzer identifying changes occurring in amplitude value and time duration in the first sweep and in the second sweep; and
   a display processor for initiating generation of at least one display image showing the first and second sweeps synchronized in time to their respective P and R waves, adjacent and mutually vertically displaced to facilitate visual comparison, said display processor highlighting the identified changes in amplitude value or time duration by a visual attribute.

2. The system of claim 1, including
a repository of information associating said identified change with an atrial or ventricular portion of a heart and wherein
said analyzer automatically uses said information in identifying a medical condition is associated with the atrial or ventricular portion of the heart in response to the identified change being associated with a P wave or an QRS complex.

3. The system of claim 2, wherein
said display processor generates another display image indicating the atrial or ventricular portion of the heart in response to identifying said medical condition.

4. The system of claim 1, wherein
said analyzer automatically sequentially analyzes a third sweep of said common portion of said plurality of successive heart cycles of the signal data, wherein the successive heart cycles in the third sweep are synchronized with respect to a Q wave.

5. The system of claim 1, wherein
said analyzer automatically sequentially analyzes a third sweep of said common portion of said plurality of successive heart cycles of the signal data, wherein the successive heart cycles in the third sweep are synchronized with respect to a S wave.

6. The system of claim 1, wherein
said analyzer automatically sequentially analyzes a third sweep of said common portion of said plurality of successive heart cycles of the signal data, wherein the successive heart cycles in the third sweep are synchronized with respect to a T wave.

7. The system of claim 1, wherein
said visual attribute comprises at least one of, (a) color, (b) highlighting, (c) shading, (d) a symbol and (e) text.

8. The system of claim 1, wherein
said analyzer sequentially automatically analyzes said first and second sweeps based on said common portion of said plurality of successive heart cycles of the signal data.

9. The system of claim 1, wherein said analyzer includes,
a signal sample and hold unit,
a peak detector for detecting signal peaks,
a time interval detector using a clock counter triggered from a synchronizing P wave or R wave peak detected by said peak detector and said analyzer automatically analyzes said first and second sweeps by comparing amplitude values captured by said sample and hold unit at corresponding time points of a plurality of successive synchronized heart cycles of the signal data.

10. The system of claim 1, wherein said analyzer includes,
a peak detector for detecting signal peaks,
a time interval detector using a clock counter triggered by a synchronizing P wave or R wave peak detected by said peak detector and terminating a count in response to an identified signal characteristic, said analyzer automatically analyzing said first and second sweeps by comparing time intervals associated with one of a plurality of different portions of a heart cycle.

11. The system of claim 1, wherein
said display processor initiates generation of the at least one display image showing the first and second sweeps of said plurality of successive heart cycles in 3-dimensions with the third dimension separating individual common portions of successive heart cycles.

12. The system of claim 1, wherein
said display processor initiates generation of the at least one display image showing the first and second sweeps of said plurality of successive heart cycles in 3-dimensions with a third dimension showing a signal property comprising at least one of (a) signal energy, (b) signal complexity, (c) signal instantaneous frequency spectrum and (d) signal latency.

13. The system of claim 1, wherein
said first or second sweep comprises a whole heart cycle or a portion less than a whole heart cycle.

14. The system of claim 1, wherein
said analyzer uses predetermined mapping information, associating ranges of said amplitude value and time duration or a value derived from said amplitude value and time duration with corresponding medical conditions, and compares said amplitude value and time duration or said value derived from said amplitude value and time duration, with said ranges and generates an alert message indicating a potential medical condition.

15. A system according to claim 14, wherein
said predetermined mapping information associates ranges of said amplitude value and time duration or a value derived from said amplitude value and time duration with particular patient demographic characteristics and with corresponding medical conditions and said analyzer uses patient demographic data including at least one of age weight, gender and height in comparing said amplitude value and time duration or a value derived from said amplitude value and time duration with said ranges and generating an alert message indicating a potential medical condition.

16. The system of claim 1, wherein
said analyzer uses predetermined mapping information, associating thresholds of said amplitude value and time duration or a value derived from said amplitude value and time duration with corresponding medical conditions, and compares said amplitude value and time duration or said value derived from said amplitude value and time duration, with said thresholds and generates an alert message indicating a potential medical condition.

17. The system of claim 1, wherein
said analyzer identifies a nonlinearity change occurring in the first and second sweeps of the plurality of successive heart cycles of the signal data.

18. The system of claim 17, wherein the said analyzer further calculates an index quantifying the identified nonlinearity change.

19. The system of claim 1, including
a repository of information associating said identified change with an interventricular portion of a heart and wherein
said analyzer automatically uses said information in identifying a medical condition is associated with the interventricular portion of the heart in response to the identified change being associated with a U wave.

20. A method for analyzing cardiac electrophysiological signals comprising the activities of:
acquiring signal data representing heart electrical activity over a plurality of heart cycles, an individual heart cycle comprising a plurality of different signal portions between successive sequential R waves;
automatically analyzing both,
a first sweep based on a common portion of a plurality of successive heart cycles of the signal data, wherein the successive heart cycles in the first sweep are synchronized with respect to a P wave, and
a second sweep based on the common portion of the plurality of successive heart cycles of the signal data, wherein the successive heart cycles in the second sweep are synchronized with respect to an R wave;
identifying changes occurring in amplitude value and time duration in the first sweep and in the second sweep;
initiating generation of at least one display image showing the first and second sweeps synchronized in time to their respective P and R waves, adjacent and mutually vertically displaced to facilitate visual comparison; and
highlighting the identified changes in amplitude value or time duration by a visual attribute.

21. The method of claim 20, including the activities of,
storing in a repository, information associating said identified change with an atrial or ventricular portion of a heart, and
automatically using said information in identifying a medical condition is associated with the atrial or ventricular portion of the heart in response to the identified change being associated with a P wave or an QRS complex.

* * * * *